(12) United States Patent
Nedden

(10) Patent No.: US 8,546,570 B2
(45) Date of Patent: Oct. 1, 2013

(54) PROCESS FOR PREPARING CATIONIC RHODIUM COMPLEXES

(75) Inventor: Hans Guenter Nedden, Cambridge (GB)

(73) Assignee: Johnson Matthey Public Limited Co., London (GB)

(*) Notice: Subject to any disclaimer, the term of this patent is extended or adjusted under 35 U.S.C. 154(b) by 69 days.

(21) Appl. No.: 13/002,434

(22) PCT Filed: Jul. 2, 2009

(86) PCT No.: PCT/GB2009/050777
§ 371 (c)(1),
(2), (4) Date: Mar. 31, 2011

(87) PCT Pub. No.: WO2010/001173
PCT Pub. Date: Jan. 7, 2010

(65) Prior Publication Data
US 2011/0190500 A1 Aug. 4, 2011

(30) Foreign Application Priority Data
Jul. 4, 2008 (GB) ................... 0812290.5

(51) Int. Cl.
*C07F 15/00* (2006.01)
*C07F 17/02* (2006.01)

(52) U.S. Cl.
USPC .................. 546/4; 556/18; 556/14; 502/162; 502/155; 502/166

(58) Field of Classification Search
None
See application file for complete search history.

(56) References Cited

U.S. PATENT DOCUMENTS

| | | | |
|---|---|---|---|
| 5,919,981 A | 7/1999 | Chan | |
| 6,720,281 B2 | 4/2004 | Leitner | |
| 6,906,212 B1 | 6/2005 | Boaz | |
| 2004/0116713 A1 | 6/2004 | Beller | |
| 2005/0228190 A1 | 10/2005 | Bao | |
| 2005/0250951 A1 | 11/2005 | Peschko et al. | |
| 2007/0004928 A1 | 1/2007 | Ramsden | |

FOREIGN PATENT DOCUMENTS

| | | |
|---|---|---|
| EP | 1127061 | 3/2003 |
| WO | 9513284 | 5/1995 |
| WO | 9747632 | 12/1997 |
| WO | 0027855 | 5/2000 |
| WO | 02026750 | 4/2002 |
| WO | 2004111065 | 12/2004 |
| WO | 2005032712 | 4/2005 |
| WO | 2008041029 | 4/2008 |
| WO | 2008084258 | 7/2008 |

OTHER PUBLICATIONS

Carretero et al., "Recent Applications of Chiral Ferrocene Ligands in Asymmetric Catalysis", Angew. Chem. Int. Ed., 2006, 45, pp. 7674-7715.
Fryzuk et al., "Asymmetric Synthesis. Production of Optically Active Amino Acids by Catalytic Hydrogenation", Journal of the American Chemical Society, 1977, 99, 6262.
Reiss et al., "Rhodium-Diphosphine Tosylate Complexes As Hydrogenation Catalysts", Collection Czechoslovak Chem. Commun., 1985, 51, 340.
Schrock et al., "Preparation and Properties of Some Cationic Complexes of Rhodium (I) and Rhodium (III)", Journal of the American Chemical Society, 1971, 93, 2397.
GB Search Report dated Nov. 4, 2008.
Tang et al., "New Chiral Phosphorus Ligands for Enantioselective Hydrogenation", Chem. Rev., 2003, 3029.
Carretero et al., "Recent Applications of Chiral Ferrocene Ligands in Asymmetric Catalysis", Angew. Chem. Int. Ed., 2006, 45, 7674.
International Search Report dated Sep. 17, 2009.

*Primary Examiner* — Mevin C Mayes
*Assistant Examiner* — Yun Qian
(74) *Attorney, Agent, or Firm* — RatnerPrestia

(57) ABSTRACT

A process is described for the synthesis of a cationic [rhodium diolefin phosphorus ligand] complex comprising the steps of: (a) reacting a rhodium-diolefin-1,3-diketonate and an acid in a ketone solvent, (b) adding a stabilising olefin to form a stabilised cationic rhodium compound, and (c) mixing a phosphorus ligand with the solution of the stabilised cationic rhodium compound to form a solution of the cationic [rhodium diolefin phosphorus ligand] complex. The solution may be used directly or the complex recovered. In one embodiment, the solution may be combined with a co-solvent and the ketone removed to give a new catalyst solution, from which the complex may be recovered.

29 Claims, No Drawings

PROCESS FOR PREPARING CATIONIC RHODIUM COMPLEXES

CROSS-REFERENCE TO RELATED APPLICATIONS

This application is the U.S. National Phase application of PCT International Application No. PCT/GB2009/050777, filed Jul. 2, 2009, and claims priority of British Patent Application No. 0812290.5, filed Jul. 4, 2008, the disclosures of both of which are incorporated herein by reference in their entirety for all purposes.

FIELD OF THE INVENTION

This invention relates to a process for preparing rhodium complexes and in particular for the large-scale manufacture of cationic [rhodium diolefin phosphorus ligand] complexes.

BACKGROUND OF THE INVENTION

[Rhodium-diolefin-phosphorus ligand] complexes find use in catalysis, for example in hydrogenation reactions, where the use increasingly requires low residual levels of impurities. In known methods, [rhodium (diolefin) halide]$_2$ starting materials have been frequently used where the halide anion has been exchanged using Ag, Tl, alkali or ammonium salts of the required anion. On applying any of these methods, we have found a variety of contaminants in the product.

In one approach, [rhodium (diolefin) halide]$_2$ is treated in the presence of further diolefin with Ag or Tl salts of the required anion forming [rhodium (diolefin)$_2$]$^+$ compounds. These rhodium compounds retain intolerable quantities of Ag or Tl residues which have a detrimental effect on storage stability. The impurities are also present when the [rhodium (diolefin)$_2$]$^+$ compounds are reacted with the phosphorus ligands to form [rhodium-diolefin-phosphorus ligand] complexes. In addition to the above problems, low yields of the complex are often obtained and whenever Ag or Tl salts are used, recovery of rhodium from the hydrogenation liquors and refinery is particularly costly because of the need to separate rhodium from the other metals during refining.

In another approach, [Rh(diolefin) halide]$_2$ is treated with the phosphorus ligand followed by alkali or ammonium salts of the required anion. The use of alkali and ammonium salts normally results in residual amounts of halide which can also limit storage stability, as well as having a detrimental effect in the catalytic application of the rhodium complex. Furthermore, the obtained [rhodium-diolefin-phosphorus ligand] complexes often contain unacceptable amounts of cationic tetracoordinate rhodium contaminants where the diolefin has been replaced by additional phosphorus ligand(s).

Another method of preparation converts [rhodium (diolefin) halide]$_2$ to halide free rhodium-diolefin-1,3-diketonate complexes using known, methods. The rhodium-diolefin-1, 3-diketonate complexes, such as Rh(diolefin)(acac), are mixed with a phosphorus ligand and a strong acid (HClO$_4$) in tetrahydrofuran solvent to obtain rhodium-diolefin-phosphorus ligand complexes (see R. Schrock, J Osborne, J. Am. Chem. Soc. 1971, 93, 2397-2407). One problem with the use of strongly coordinating ethereal solvents such as tetrahydrofuran (THF) has been observed by M. D. Fryzuk and B. Bosnich who used [Rh nbd acac] in THF for the synthesis of [Rh nbd (S,S)-Chiraphos]ClO$_4$ THF adduct (see J. Am. Chem. Soc. 1977, 99, 6262-6267). A THF adduct of the complex was obtained and it proved impossible to remove the THF from the obtained complex.

WO 2005/032712 discloses a method for preparing rhodium phosphine complexes comprising the steps of (a) dissolving Rh(diolefin)(acac) in a strongly coordinating ethereal solvents such as tetrahydrofuran (THF) and additional ethereal solvents such as diethyl ether or methyl tert-butyl ether (MTBE) (b) adding to this a fluorinated non-mineral acid HX, such as a tetrafluoroboric acid etherate, and alcohol solvent or alcohol containing solvent mixture, either simultaneously or sequentially, to form a soluble solvated complex of rhodium with one or more of the reaction solvents, (c) adding the phosphorus ligand, either in solution in an organic solvent or neat, and (d) collecting the crystalline precipitate. This procedure is not satisfactory because two ether solvents are required in addition to the alcoholic solvent and a number of the examples describe crystallisation processes at very low temperatures such as −20 to −30° C.

EP1127061B1 discloses a procedure for the preparation of slurries of [Rh(COD)$_2$]BF$_4$ from a solution of Rh(COD)acac in THF. The procedure is difficult to scale up because the slurry of [Rh(COD)$_2$]BF$_4$ intermediate precipitates from THF and it is extremely difficult to agitate on a large scale. After the addition of the phosphorus ligand, the soluble cationic [rhodium diolefin phosphorus ligand] complex is precipitated by adding ethereal anti-solvents like MTBE and diethyl ether.

SUMMARY OF THE INVENTION

We have developed a process that is more suited to large-scale manufacture of cationic [rhodium diolefin phosphorus ligand] complexes from rhodium-diolefin-1,3-diketonate starting materials in a procedure that yields solutions of the complex in a solvent more suitable than those of the prior art processes.

Accordingly, the invention provides a process for the synthesis of a cationic [rhodium diolefin phosphorus ligand] complex comprising the steps of:
  (a) reacting a rhodium-diolefin-1,3-diketonate and an acid in a ketone solvent,
  (b) adding a stabilising olefin to form a stabilised cationic rhodium compound, and
  (c) mixing a phosphorus ligand with the solution of the stabilised cationic rhodium compound to form a solution of the cationic [rhodium diolefin phosphorus ligand] complex.

DETAILED DESCRIPTION OF THE INVENTION

Preferably, the rhodium-diolefin-1,3-diketonate contains a cyclic diolefin, more preferably 2,5-norbornadiene (NBD) or 1,5-cyclooctadiene (COD). Alternatively the cyclic diolefin can be replaced by either 2 molecules of an olefin such as ethylene or 2 molecules of a $C_{5-10}$ cycloalkene.

Preferably, the rhodium-diolefin-1,3-diketonate compound contains coordinated acetylacetonate and similar 1,5 substituted acetylacetonate ligands such as hexafluoroacetylacetonate or 1,5-dimethylacetylacetonate. More preferably the 1,3-diketonate is acetylacetonate. Most preferably, the rhodium-diolefin-1,3-diketonate compound is rhodium cyclooctadiene acetylacetonate, Rh(COD)(acac). Rh(COD)(acac) is available commercially or may be synthesised using known methods.

The acid used is preferably a perfluorinated acid in order to provide a perfluorinated anion. Preferred perfluorinated acids are tetrafluoroboric acid (HBF$_4$), trifluoromethanesulfonic acid (CF$_3$SO$_3$H), hexafluorophosphoric acid (HPF$_6$), hexafluoroantimonic acid HSbF$_6$ and perfluoro alkylsulfonic acids e.g. heptadecafluorooctanesulfonic acid. Most preferred are tetrafluoroboric acid ($HBF_4$) and trifluoromethanesulfonic acid ($CF_3SO_3H$). In a preferred embodiment, the acid is diluted with ketone solvent and then added to the reaction mixture. Less preferred for larger scale manufacture is the addition of the neat acid. Tetrafluoroboric acid may be used in liquid form as the diethyletherate. In some cases, where the phosphorus ligand is resistant to hydrolysis aqueous tetrafluoroboric acid solutions may be used, which are easier to handle and use than tetrafluoroboric acid diethyletherate.

The rhodium-diolefin-1,3-diketonate compound and acid are combined in a ketone solvent. By "ketone solvent" we mean a liquid ketone that is able to dissolve the rhodium-diolefin-1,3-diketonate compound to form solutions that are preferably in the range of 0.01-1 molar. Suitable ketone solvents have boiling points at atmospheric pressure (i.e. $1.0135 \times 10^5$ Pa) below 160° C. and more preferably below 120° C. Preferred examples are acetone, methyl-ethyl ketone (MEK) also known as 2-butanone, methyl-isobutyl ketone (MIBK) also known as 4-methyl-2-pentanone and diethylketone also known as 3-pentanone. A particularly preferred ketone solvent is MEK. Another particularly preferred ketone solvent is acetone.

There are several advantages associated with using a ketone solvent. One advantage is that the cationic [rhodium diolefin phosphorus ligand] complex may be used as catalysts in hydrogenation reactions without the requirement of a solvent change. Another advantage is the possibility of isolating ether solvate complexes other than THF solvates from mixtures of solvent and ether.

In combining the rhodium-diolefin-1,3-diketonate compound and acid in the ketone solvent, the components may be mixed in any order, although preferably the rhodium diolefin 1,3-diketonate is first dissolved in ketone and then the acid is added.

An amount of a stabilising olefin is added to the combination of the rhodium-diolefin-1,3-diketonate and acid in the ketone solvent to form a stabilised cationic rhodium compound. By "stabilising" or "stabilised" we mean an olefin which comprises at least one carbon-carbon double bond (C=C) and coordinates to the [rhodium diolefin] fragment. While not wishing to be bound by theory, it is believed the phosphorus ligand will coordinate to a free [rhodium diolefin] fragment with different kinetics as compared to the displacement of a coordinated olefin. Accordingly, the stabilising olefin will have a moderating and inhibiting effect on the reaction between the phosphorus ligand and the cationic [rhodium diolefin] fragment. It is believed that this will result in a more selective reaction with the consequence that less impurities are produced.

Preferably, the stabilising olefin comprises one or two carbon-carbon double bonds. When the stabilising olefin has one carbon-carbon double bond, the stabilising olefin is preferably a cyclic monoolefin. Preferably, the cyclic monoolefin is a substituted or unsubstituted $C_5$-$C_{12}$ cyclic monoolefin, such as substituted or unsubstituted cyclopentene, substituted or unsubstituted norbornene, substituted or unsubstituted cyclohexene, substituted or unsubstituted cycloheptene or substituted or unsubstituted cyclooctene. The substituting group is preferably one, two or more $C_1$-$C_5$ alkyl groups. The alkyl groups may be branched or straight chain alkyl groups. Most preferably, the cyclic monoolefins are selected from the group consisting of cyclopentene, 1-methyl-1-cyclopentene, norbornene (i.e. bicycle[2.2.1]hept-2-ene), cyclohexene, 1-methyl-1-cyclohexene, 1,2-dimethyl-1-cyclohexene, cycloheptene and cyclooctene. In a preferred embodiment, the cyclic monoolefin is cyclooctene. The amount of the cyclic monoolefin may be in the range of 1 to 250%, preferably 1 to 200% of the molar quantity of the rhodium diolefin 1,3-diketonate compound.

Alternatively, when the stabilising olefin has two carbon-carbon double bonds, the stabilising olefin is preferably a cyclic diolefin, more preferably 2,5-norbornadiene (NBD) or 1,5-cyclooctadiene (COD). Most preferably, the corresponding diolefin to that in the rhodium compound is preferably used and so in a preferred embodiment 2,5-norbornadiene (NBD) is added to reactions using Rh(NBD) 1,3-diketonate compounds and 1,5-cyclooctadiene (COD) is added to reactions with Rh(COD) 1,3-diketonate compounds. The amount of the cyclic diolefin may be in the range 1 to 200%, preferably 1 to 100% of the molar quantity of the rhodium diolefin 1,3-diketonate compound.

After the addition of the stabilising olefin, preferably the mixture is stirred at a temperature in the range −20 to 70° C., preferably −10 to 60° C. and most preferably 0 to 50° C. The mixture may be stirred for a period e.g. preferably 1 minute to 3 hours, more preferably 2 minutes to 1.5 hours and most preferably 2.5 minutes to 1 hour. A cationic rhodium compound in a ketone solvent is formed. When the stabilising olefin comprises two C=C bonds, the cationic rhodium compound is $[Rh(diolefin)_2]^+ [X]^-$, where $[X]^-$ is an anion derived from the acid.

A phosphorus ligand is added to the solution of the cationic rhodium compound formed in the previous step. Any suitable phosphorus compound capable of forming a ligand-metal interaction with the Rh atom may be used. In the ligand, each phosphorus atom is covalently bonded to either 3 carbon atoms (tertiary phosphines) or to n heteroatoms and 3-n carbon atoms, where n=1, 2 or 3. Preferably, the heteroatom is selected from the group consisting of N and O.

The phosphorus ligand may be monodentate, e.g. $PPh_3$, or bidentate. The ligand may be chiral or achiral, although in many instances it is preferred that the phosphorus ligand is chiral. A variety of chiral phosphorus ligands has been described and reviews are available, for example see W. Tang and X. Zhang, Chem. Rev. 2003, 103, 3029-3070 and J. C. Carretero, Angew. Chem. Int. Ed., 2006, 45, 7674-7715. Phosphorus ligands that may be used in the present invention include but are not restricted to the following structural types:

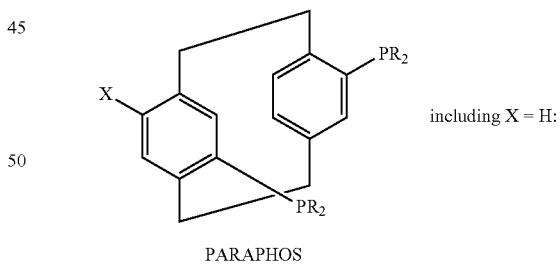

PARAPHOS

X = functional group
R = aryl, alkyl

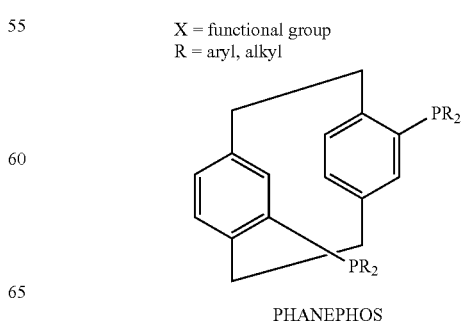

PHANEPHOS

-continued

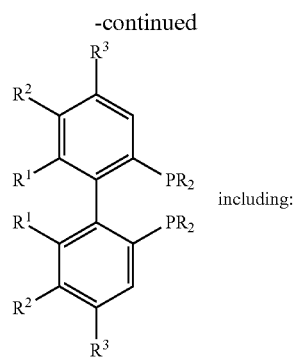

Substituted Biphenyl:

R = aryl and alkyl
R$^1$ = alkyl, alkoxy
R$^2$ = H, alkyl, alkoxy, halide
R$^3$ = H, alkyl

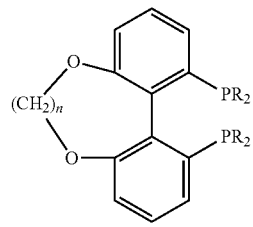

C$_n$ TUNAPHOS

R$^1$ = OMe: BIPHEP
R$^1$ = OMe, R$^2$ = Cl: Cl, MeO BIPHEP
R$^1$ and R$^3$ = Me, R$^2$ = OMe: BIMOP
R$^1$ = Me: BIPHEMP
R$^1$ and R$^3$ = Me: TETRAPHEMP
R$^1$, R$^2$ and R$^3$ = Me: HEXAPHEMP

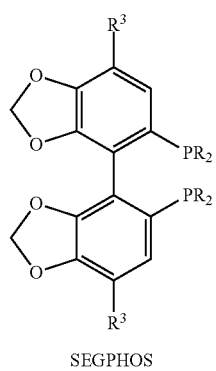

SEGPHOS

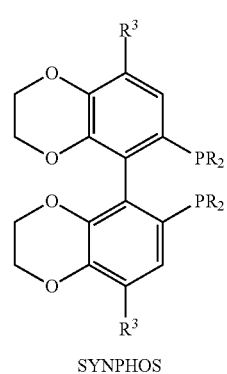

SYNPHOS

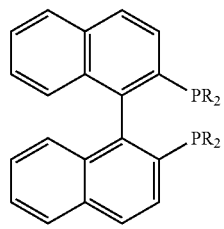

BINAP, R = aryl and alkyl

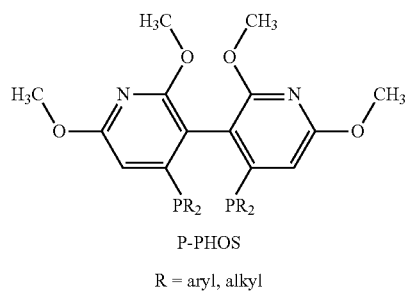

P-PHOS

R = aryl, alkyl

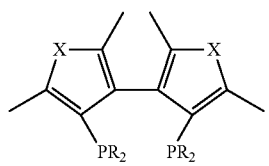

TMBITIOP

R = aryl, alkyl
X = O, S, N

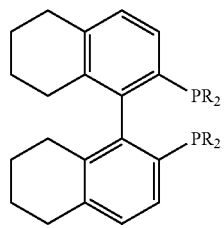

H$^8$-BINAP,

R = aryl and alkyl

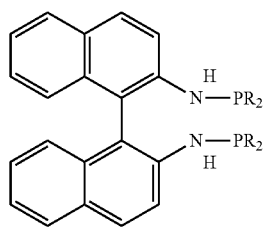

BINAM-P,

R = aryl, alkyl and Oaryl, Oalkyl

-continued

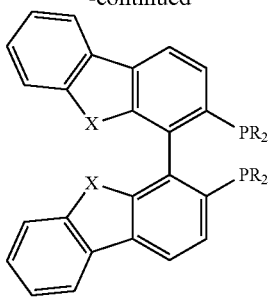

R = aryl, alkyl
X = O BIBFUP
X = NH or S

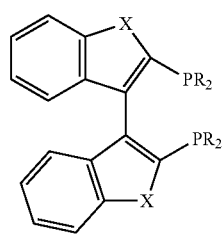

BITIANAP

R = aryl, alkyl
X = O, S, N

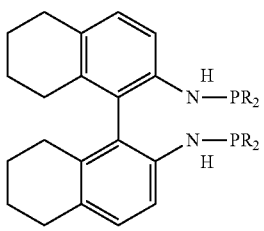

$H^8$-BINAM-P,

R = aryl, alkyl and Oaryl, Oalkyl

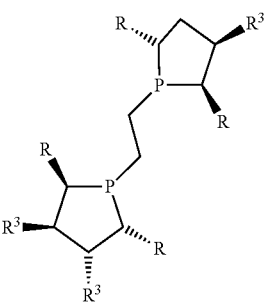

BPE-type

R = alkyl, aryl, $CH_2OR^2$
$R^3$ = H or $OR^2$
$R^2$ = alkyl

-continued

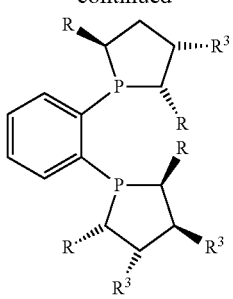

DUPHOS-type

R = alkyl, $CH_2OR^2$
$R^3$ = H or $OR^2$
$R^2$ = alkyl

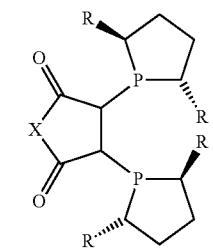

MALPHOS type

X = O, NR

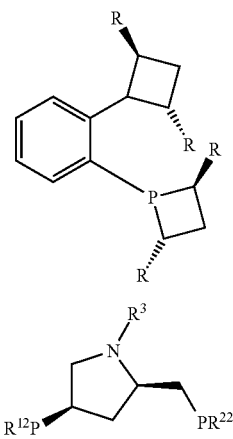

BPPM $R^1$ = alkyl, aryl
$R^2$ = alkyl, aryl
$R^3$ = substituted alkyl

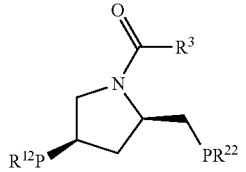

BPPM amide $R^1$ = alkyl, aryl
$R^2$ = alkyl, aryl
$R^3$ = alkyl, aryl, $OR^4$, $NR^4_2$
$R^4$ = alkyl, aryl -continued

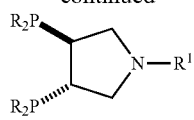

DEGPHOS

R = aryl
R¹ = (substituted) alkyl
R² = alkyl, aryl

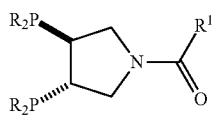

DEGPHOS amide

R = aryl
R¹ = alkyl, aryl, OR², NR²₂
R² = alkyl, aryl

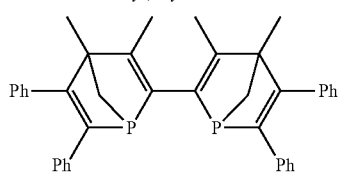

BIPNOR

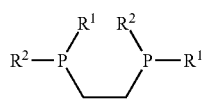

DIPAMP

R¹ = phenyl
R² = 4-MeO-phenyl

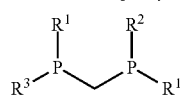

TCFP

R¹ = R² = tert-Bu
R³ = Me

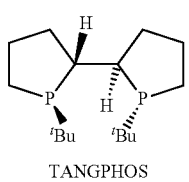

TANGPHOS

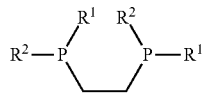

MINIPHOS

R¹ different from R²
R¹, R² alkyl or aryl

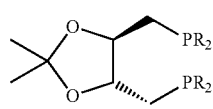

DIOP

R = alkyl, aryl

-continued

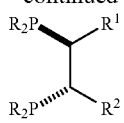

CHIRAPHOS

R¹ = R² alkyl

PROPHOS

R² = alkyl R¹ = H

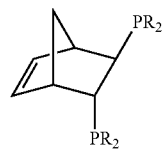

(Re)-Norphos
R = alkyl, aryl

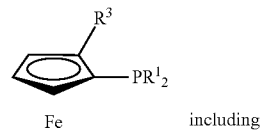

including

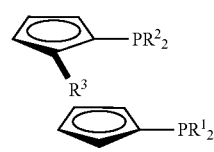

DIPFC: R¹ = R² = ˢᵉᶜPr
DCyPFC: R¹ = R² = Cy

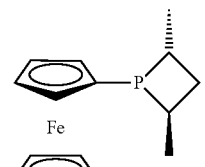

Me - FERROTANE

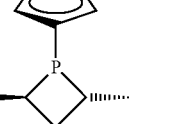

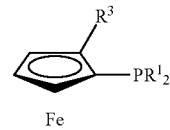

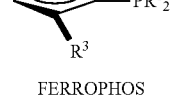

FERROPHOS

R¹ = alkyl, aryl
R³ = 3-pentyl

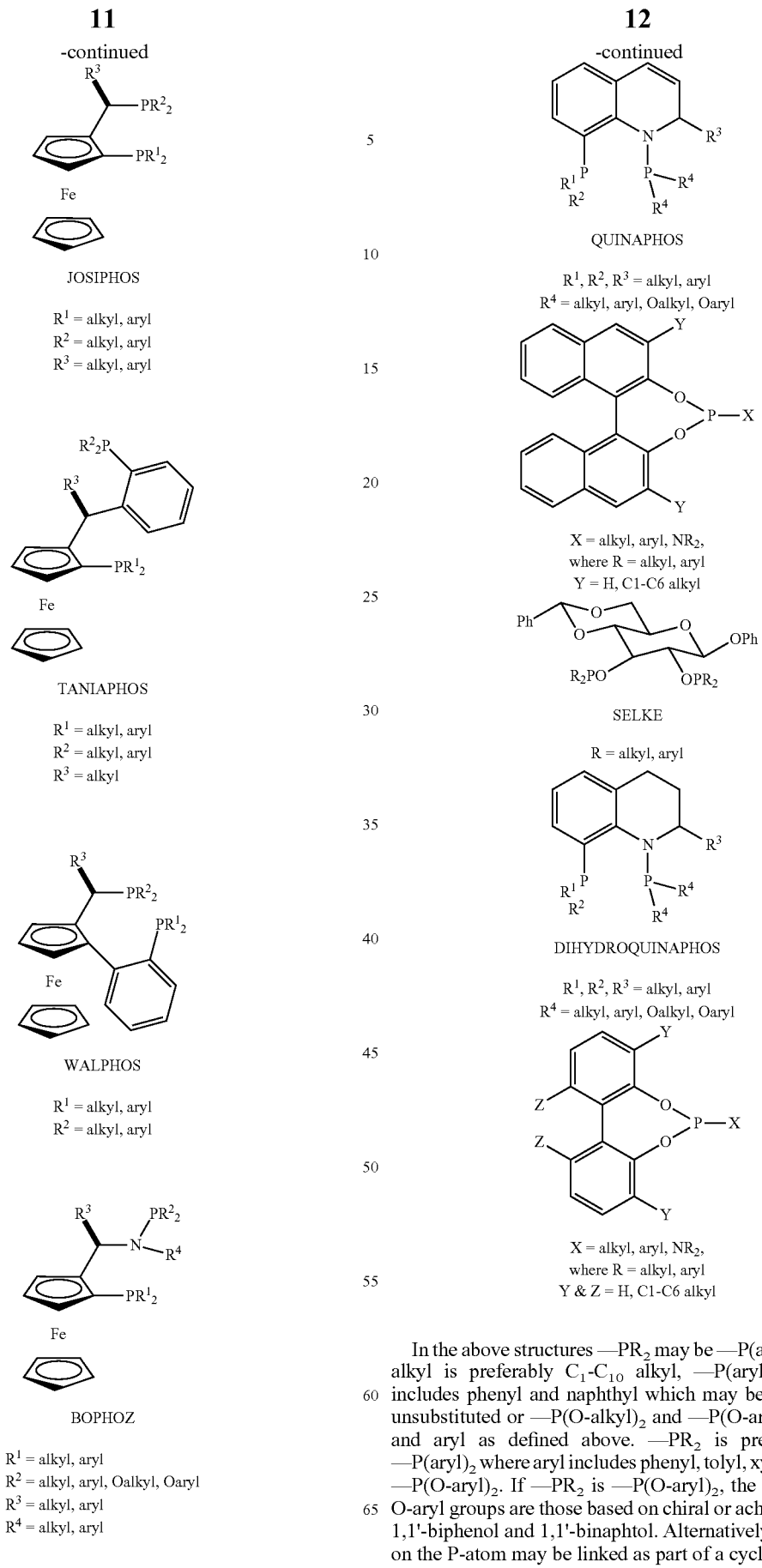

In the above structures —PR$_2$ may be —P(alkyl)$_2$ in which alkyl is preferably C$_1$-C$_{10}$ alkyl, —P(aryl)$_2$ where aryl includes phenyl and naphthyl which may be substituted or unsubstituted or —P(O-alkyl)$_2$ and —P(O-aryl)$_2$ with alkyl and aryl as defined above. —PR$_2$ is preferably either —P(aryl)$_2$ where aryl includes phenyl, tolyl, xylyl or anisyl or —P(O-aryl)$_2$. If —PR$_2$ is —P(O-aryl)$_2$, the most preferred O-aryl groups are those based on chiral or achiral substituted 1,1'-biphenol and 1,1'-binaphtol. Alternatively, the R groups on the P-atom may be linked as part of a cyclic structure.

Substituting groups may be present on the alkyl or aryl substituents in the phosphorus ligands. Such substituting groups are typically branched or linear $C_{1-6}$ alkyl groups such as methyl, ethyl, propyl, isopropyl, tert butyl and cyclohexyl.

The phosphorus ligands are preferably used in their single enantiomer form. These phosphorus ligands are generally available commercially and their preparation is known. For example, the preparation of PARAPHOS ligands is given in WO 04/111065, the preparation of Bophoz ligands in WO02/26750 and U.S. Pat. No. 6,906,212, the preparation of QUINAPHOS ligands in U.S. Pat. No. 6,720,281, the preparation of $H^8$-BinamP ligands in U.S. Pat. No. 5,919,981 and the preparation of Dihydroquinaphos ligands in WO2008/041029.

Preferred phosphorus ligands include substituted or unsubstituted $P(phenyl)_3$, Binap, DPEPhos, PPhos ligands, Phanephos, Bophoz ligands, BinamP, $H^8$-BinamP, Quinaphos, Selke ligands, DIPAMP, DPPE, TCFP, Dihydroquinaphos, Monophos, DIPFC and DCyPFC, which may be substituted as indicated above.

Upon mixing the phosphorus ligand with the solution of cationic rhodium compound, a clear solution of the cationic [rhodium diolefin phosphorus ligand] complex is obtained. If desired, the solution may be heated to a temperature in the range 20-70° C., preferably >40° C., e.g. 40-70° C. for a period, e.g. between 1 minute and 8 hours, preferably 1 minute and 3 hours, to ensure complete reaction between the cationic rhodium compound and phosphorus ligand.

The solution of the cationic [rhodium diolefin phosphorus ligand] complex in the ketone may be used directly, if the application requires a ketone solvent.

However, it may be desirable to recover the cationic [rhodium diolefin phosphorus ligand] complex, in which case the process of the present invention may further comprise:
(i) evaporating at least a portion of the ketone solvent from the solution obtained in step (c) to form a slurry or a concentrated solution of the cationic [rhodium diolefin phosphorus ligand] complex,
(ii) optionally treating the resulting solution of the complex with an anti-solvent selected from low boiling ethers or alkanes to precipitate the complex,
(iii) recovering the cationic [rhodium diolefin phosphorus ligand] complex as a solid, and
(iv) optionally slurrying the solid cationic [rhodium diolefin phosphorus ligand] complex in an anti-solvent selected from low boiling ethers or alkanes and repeating step (iii).

In step (i) the ketone solvent is at least partially removed in order to increase the concentration of cationic [rhodium diolefin phosphorus ligand] complex. By the term "concentrated solution" we mean a concentration of the cationic [rhodium diolefin phosphorus ligand] complex is preferably 0.5 moles/litre, more preferably >1 mole/litre. This may be achieved by increasing the temperature or reducing the pressure using distillation or stripping methods well known in the art. The complex is preferably recovered as crystalline product. Accordingly, the solution may be heated under vacuum to remove ketone solvent until crystallisation of the complex occurs, but is not continued until all the solvent is removed. In this way, the product after evaporation of ketone solvent is a slurry of crystalline cationic [rhodium diolefin phosphorus ligand] complex in a remaining portion of the ketone solvent. The crystallisation can be induced at temperatures between −40° C. and 100° C., more preferably between 0° C. and 80° C. and most preferably between 0° C. and 50° C.

Alternatively, the ketone solvent may be removed (for example, by distillation or stripping methods) from the solution of cationic [rhodium diolefin phosphorus ligand] complex until a very concentrated solution of the cationic [rhodium diolefin phosphorus ligand] complex in a remaining portion of the ketone solvent is obtained. Then, an anti-solvent selected from low boiling ethers or alkanes may be added to cause precipitation of the complex. Suitable ethers have boiling points at atmospheric pressure between −30 to 120° C. Ethers that may be used as anti-solvents are weakly coordinating ethers such as dialkyl ethers, e.g. dimethyl ether, diethyl ether, dipropyl ether, diisopropyl ether or methyl-tert-butyl ether (MTBE), or 5- or 6-membered cycloalkyl ethers e.g. 1,3-dioxolane, tetrahydropyran, 1,3-dioxane or 1,4-dioxane. Preferably, the ether is selected from the group consisting of diethyl ether, MTBE and 1,4-dioxane.

Suitable alkanes have boiling points at atmospheric pressure between 0 to 150° C. Alkanes that may be used are low boiling alkanes such as pentane isomers, hexane isomers, heptane isomers or octane isomers. Preferably, the alkane is n-pentane, n-hexane or n-heptane.

The [rhodium diolefin phosphorus ligand] complex product may be recovered directly by filtrating, decanting or centrifuging. The complex thus obtained may contain coordinated ketone solvent. Hence, the complexes thus obtained are particularly suitable as catalysts for applications using ketone solvents. If desired, the solid [rhodium diolefin phosphorus ligand] complex may then be reslurried in an anti-solvent and the complex recovered by filtering, decanting or centrifuging as described above.

The [rhodium diolefin phosphorus ligand] complex product may however also be used as catalysts for applications using alcohol, chlorinated hydrocarbon, aromatic hydrocarbon and ester solvents. In this case it may be desirable to first partially strip a solution of the recovered complex in the selected solvent in order to remove remaining ketone and, any anti-solvent, prior to the catalytic step. For example, we have found that that residual ketone and anti-solvents can be removed by partially stripping a solution of the [rhodium diolefin phosphorus ligand] complex in dichloromethane. If desired, a small amount of stabilising olefin may be added to the solvent prior to stripping to maintain the stability of the complex during this process.

However, as an alternative to the above recovery methods, it is more desirable to completely replace the ketone solvent of the cationic [rhodium diolefin phosphorus ligand] complex with a solvent of the intended application and to use this solution or to recover the complex from this solution so that any amount of solvent residue that remains in the recovered complex is tolerable for the catalytic application and/or for its storage stability.

In such cases, the ketone solvent chosen for steps (a) and (c) is preferably selected so that it may at least be partially removed by distillation in the presence of a co-solvent, in particular a co-solvent that is desirable in the foreseen use of the complex as a catalyst. Accordingly, in one preferred embodiment of the present invention, the process further comprises:
(i) optionally evaporating at least a portion of the ketone solvent from the solution obtained in step (c) to form a slurry or a concentrated solution of the cationic [rhodium diolefin phosphorus ligand] complex,
(ii) adding to the solution obtained in step (c), or to the slurry or concentrated solution obtained in (i), a suitable amount of a co-solvent, and
(iii) evaporating at least a portion of the ketone solvent/co-solvent mixture to obtain a slurry or concentrated solution of the cationic [rhodium diolefin phosphorus ligand] complex.

A variety of co-solvents may be used depending upon the foreseen end-use of the complex. Co-solvents may be at least one of alcohols, weakly-coordinating ethers, esters, chlorinated hydrocarbons and others. Using alcohols as co-solvents is preferred to ethers. Ethers that may be used are those that are described above. Preferably, the ethers are weakly coordinating ethers such as dialkyl ethers, e.g. diethyl ether or methyl-tert-butyl ether (MTBE) or cycloalkyl ethers e.g. 1,4-dioxane. Suitable alcohols have boiling points at atmospheric pressure below 165° C. and more preferred below 135° C. Preferred examples are methanol, ethanol, 2-propanol also known as IPA, 1-butanol, 2-butanol, 3-methyl-2-butanol, 2-methyl-2-butanol also known as t-amyl alcohol, 3-methyl-1-butanol also known as iso-amyl alcohol. Particularly preferred co-solvents are ethanol and iso-propanol.

It is preferred to use an alcohol with a higher boiling point than the ketone solvent. The amount of alcohol is preferably in excess of the residual ketone solvent in the solution or slurry of the rhodium complex, preferably ≥1:1 by volume, more preferably between 1:1 and 8:1 by volume based on the ketone solvent. Preferably, the alcohol solvent is the one to be used in the subsequent catalytic application of the complex. However, the use of methanol can reduce isolated yields and therefore in this case it may then be preferred to isolate the cationic rhodium complex using another alcohol solvent with a similar boiling point, e.g. ethanol, and to re-crystallise the wet isolated cationic rhodium complex using methanol.

If it is desired to recover the rhodium complex, the process preferably further comprises:
(iv) crystallising at least one crop of the complex from the solution of co-solvent at temperatures between −40° C. and 100° C., preferably between 0° C. and 80° C. and most preferably between 0° C. and 50° C., and
(v) recovering the cationic [rhodium diolefin phosphorus ligand] complex as a solid.

The cationic [rhodium diolefin phosphorus ligand] complex product may be recovered directly by filtering, decanting or centrifuging. If desired a proportion of the co-solvent and any residual ketone or ether may be evaporated prior to recovery of the complex. Furthermore, if desired an anti-solvent may be used to precipitate the complex from the co-solvent.

Howsoever the complex is recovered, the separated complex is preferably washed with cold alcohol and then dried. Drying may be performed using known methods, for example at temperatures in the range 10-60° C. and preferably 20-40° C. under 1-30 mbar vacuum for 1 hour to 5 days. If desired the complex may be recrystallised.

If desired, the process may further comprise:
(vi) treating the solid cationic [rhodium diolefin phosphorus ligand] complex with a co-solvent, anti-solvent or mixture thereof, wherein the co-solvent may be the same or different to the co-solvent in step (iv);
(vii) concentrating the solution of the cationic [rhodium diolefin phosphorus ligand] complex; and
(viii) optionally repeating steps (iv) and (v).

It may be desirable to form a cationic [rhodium phosphorus ligand]$_2$ complex, in which case the process of the present invention further comprises:
(a') forming a solution of the cationic [rhodium diolefin phosphorus ligand] complex in a ketone solvent if required,
(b') hydrogenating the solution of the cationic [rhodium diolefin phosphorus ligand] complex, and
(c') recovering cationic [rhodium phosphorus ligand]$_2$ complex as a solid.

Alternatively, it may be desirable to form a cationic [rhodium arene phosphorus ligand] complex or a cationic [rhodium (phosphorus ligand)$_2$] complex, in which case the process of the present invention further comprises:
(a') forming a solution of the cationic [rhodium diolefin phosphorus ligand] complex in a ketone solvent if required,
(b') adding an arene or a phosphorus ligand to the solution of the cationic [rhodium diolefin phosphorus ligand] complex,
(c') hydrogenating the mixture of step (b'), and
(d') recovering as a solid cationic [rhodium arene phosphorus ligand] complex or cationic [rhodium (phosphorus ligand)$_2$] complex.

The solution of the cationic [rhodium diolefin phosphine ligand] complex in the ketone may be used directly. Alternatively, a solution of the solid cationic [rhodium diolefin phosphine ligand] complex may be formed by the addition of a ketone solvent. Suitable ketone solvents are described above. The solution of the cationic [rhodium diolefin phosphine ligand] complex is preferably purged with an inert gas e.g. nitrogen or argon prior to reacting with hydrogen.

When present, the arene may be selected from a substituted or unsubstituted benzene. The substituting group is preferably one or more branched or unbranched $C_{1-5}$-alkyl groups and more preferably methyl. In a preferred embodiment, the arene is selected from the group consisting of benzene, toluene, xylene isomers, trimethylbenzene isomers and hexamethylbenzene. Alternatively, when present, the phosphorus ligand may be the same as or different to the phosphorus ligand chosen to form the cationic [rhodium diolefin phosphorus ligand] complex. Suitable phosphorus ligands are described above.

Preferably, the solution of the cationic [rhodium diolefin phosphorus ligand] complex, with or without the arene or phosphorus ligand, is reacted with hydrogen for a period e.g. between 1 minute to 10 hours, preferably 1 to 5 hours and most preferably between 2 to 3 hours. Preferably, the reaction is carried out at a temperature of 0 to 50° C., more preferably 10 to 40° C. and most preferably 20 to 30° C. In a particularly preferred embodiment, the reaction is carried out at room temperature. Preferably, the pressure under which the reaction is conducted is 0.01 to 50 bar, more preferably 0.01 to 30 bar and most preferably 3 to 25 bar.

The solid complexes may be recovered by filtering, decanting or centrifuging. If desired a proportion of the ketone solvent may be evaporated prior to the recovery of the complex. Furthermore, if desired an anti-solvent may be used to precipitate the complex from the co-solvent.

The catalysts obtained by the method of the present invention are pure and may, depending upon the final choice of solvent, contain very low or no ether residues, e.g. <0.1% wt ethers, but may contain small amounts of a residual alcohol. The catalysts can be used in catalytic applications as obtained or further dried. We have found that alcohols are easier to remove than ethers upon drying under vacuum. Furthermore the catalysts obtained using the present method are easy to filter and therefore are suited to large-scale manufacture.

EXAMPLES

The invention is further illustrated by reference to the following non-limiting examples.

Comparative Example 1

0.525 g (1.058 mmol) of [Rh(COD)Cl]$_2$ was mixed with 6 ml of dry methanol and 1 ml of water in a 50 ml Schlenk flask. To this solution was added 0.971 g (2.116 mmol) of (S,S)-

DIPAMP in portions over the period of 30 min. After stirring for 1 hour the red-orange solution was filtered to remove traces of insolubles and a solution of 0.45 g of sodium tetrafluoroborate in 4 ml of water was added to the filtered solution over a period of 20 minutes. A slurry formed after adding about 1 ml of the aqueous solution. The resulting slurry was degassed and stirred at 25° C. for 2 hours. Then the slurry was added 5 ml of water and the mixture was filtered and washed with aqueous methanol (50% vol/vol) and water. After drying for 3 hours (1 mbar, 40° C.) 1.42 g of orange solid was obtained.

The product [Rh cod(S,S)-DIPAMP]BF$_4$ was contaminated with 7% of [Rh((S,S)-DIPAMP)$_2$]BF$_4$($^1$H and $^{31}$P NMR). Recrystallisation was shown to purify the product but overall yield dropped dramatically.

In addition to NMR evidence a sample of [Rh cod(S,S)-DIPAMP]BF$_4$ contaminated with 11% of [Rh((S,S)-DIPAMP)$_2$]BF$_4$ was dissolved in d$^4$ methanol and a small amount of (S,S)-DIPAMP was added as a solid. The $^1$H and $^{31}$P NMR of the resulting solution showed that the (S,S)-DIPAMP had reacted to form a mixture of [Rh cod(S,S)-DIPAMP]BF$_4$ contaminated with 50% of [Rh((S,S)-DIPAMP)$_2$]BF$_4$.

Further reactions, starting from mixtures of [Rh(COD)Cl]$_2$ and (S,S)-DIPAMP in aqueous and non-aqueous methanol and adding [Rh(COD)Cl]$_2$ to (S,S)-DIPAMP in aqueous and non-aqueous methanol gave compositions of [Rh cod(S,S)-DIPAMP]BF$_4$ contaminated with up to 30% of [Rh((S,S)-DIPAMP)$_2$]BF$_4$.

Comparative Example 2

1.24 g (3.98 mmol) of Rh(COD)(acac) was dissolved with 8 ml of THF in a 0.1 litre Schlenk flask. To this 0.5 N solution was added 0.97 ml (8.02 mmol, 2 eq) of 1,5-cyclooctadiene by syringe. The mixture was heated to 50° C. (oil bath) and a mixture of 4 ml of THF and 0.56 ml of neat 54% wt tetrafluoroboric acid in diethylether (4.05 mmol) was added by syringe. A slurry of Rh(COD)$_2$BF$_4$ was formed immediately that could be stirred only after the addition of further 4 ml of THF. The slurry was cooled in an ice bath to 0° C. and a solution of 1.83 g (3.99 mmol) of (S,S)-DIPAMP in 15 ml of THF was added over 10 minutes by syringe. Further 5 ml of THF were required to rinse the residues in the syringe into the reaction mixture. After 15 minutes stirring the clear red solution was partially stripped until a slurry containing 5 ml of solvent remained. At this point the slurry was filtered, and the solid washed with 3 ml of cold THF. After drying 15 hours (1 mbar, 20° C.), 2.55 g of pure complex [Rh cod(S,S)-DIPAMP]BF$_4$ crystallising with 0.75 mol of THF.

Addition of diethyl ether to the mother liquor gave further product [Rh cod(S,S)-DIPAMP]BF$_4$ crystallising with 0.75 mol of THF (0.4 g). This was contaminated with [Rh((S,S)-DIPAMP)$_2$]BF$_4$.

Comparative Example 3

Solvent Screening:

0.309 g (0.995 mmol) of Rh(COD)(acac) was dissolved with 2 ml of THF in a small Schlenk flask. To this 0.5 N solution was added 0.25 ml (2.05 mmol, 2 eq) of 1,5-cyclooctadiene by syringe. The mixture was heated to 50° C. (oil bath) and a mixture of 2 ml of an solvent A (see table) and 0.14 ml of neat 54% wt tetrafluoroboric acid in diethylether (1.05 mmol) was added by syringe. A slurry of Rh(COD)$_2$BF$_4$ was formed immediately that could be stirred only after the addition of further 1 ml of solvent A. The slurry was cooled in an ice bath to 0° C. and a solution of 0.458 g (0.99 mmol) of (S,S)-DIPAMP in 2 ml of THF was added over 3 minutes by syringe. A slurry was obtained, which was partially stripped, filtered, and the solid washed with 1/1 mixtures of solvent A and THF. The THF solvates were dried (4 days, 1 mbar, 20° C.) and the composition was analysed by NMR. Isolated yields were above 90%

| Entry | Solvent A | Content [Rh ((S,S)-DIPAMP)$_2$]BF$_4$ | Solvent content |
|---|---|---|---|
| 1 | Diethyl ether | 2% | 0.75 eq THF |
| 2 | MTBE | 1% | 0.6 eq THF |
| 3 | 1,4-Dioxane | 8% | 0.6 eq dioxane 0.15 eq THF |

Example 1

1.24 g (3.98 mmol) of Rh(COD)(acac) was dissolved in 22 ml of MEK in a 0.1 litre Schlenk flask. To the resulting clear solution was added 0.56 ml of neat 54% wt tetrafluoroboric acid in diethylether (4.05 mmol) by syringe over a period of 5 minutes, resulting in a red solution. After 10 minutes, 0.26 ml (2.23 mmol) of 1,5-cyclooctadiene was added by syringe. The brown red slurry was stirred for 10 minutes and then cooled in an ice bath to 0° C. Then 1.83 g (3.99 mmol) of (S,S)-DIPAMP was added as a solid. 3 ml of MEK were required to rinse the addition funnel. After 2 minutes stirring a clear orange solution resulted. To the stirred solution was then added 10 ml of 1,4-dioxane resulting in the formation of a slurry that was partially stripped until 10 ml of solvent remained. At this point the solid was filtered, and the solid washed with a mixture of 3 ml of MEK and 3 ml of dioxane. After drying overnight (1 mbar, 20° C.) 1.36 g of complex pure [Rh cod(S,S)-DIPAMP]BF$_4$ crystallising with 0.75 mol of dioxane were obtained. Further drying (5 d, 1 mbar, 20° C.) did not change the solvent content. Yield=45% (1.8 mmol).

The combined MEK/dioxane solutions were further stripped and an excess of 20 ml of heptane was added. The resulting slurry was filtered, washed with a mixture of 5 ml heptane/1 ml of MEK and dried overnight (1 mbar, 20° C.). After drying overnight (1 mbar, 20° C.) 1.62 g of complex [Rh cod(S,S)-DIPAMP]BF$_4$ crystallising with 0.33 mol of dioxane and approximately 0.2 eq of MEK were obtained. Only traces of [Rh((S,S)-DIPAMP)$_2$]BF$_4$ were present. Further drying (5 d, 1 mbar, 20° C.) did not change the solvent content and the approximately 0.2 eq of MEK were retained. Yield=54% (2.15 mmol). The preparation of dioxane solvates free of THF is not possible by the method of Comparative Example 3.

Example 2

Solvent Screening: 0.309 g (0.995 mmol) of Rh(COD)(acac) was dissolved with 6 ml of MEK in a small Schlenk flask. To the resulting clear solution was added 0.14 ml of neat 54% wt tetrafluoroboric acid in diethylether (1.05 mmol) by syringe over a period of 5 minutes, resulting in a red solution. After 3 minutes, 0.07 ml (0.056 mmol) of 1,5-cyclooctadiene was added by syringe. The brown red slurry was stirred for 3 minutes and then cooled in an ice bath to 0° C. Then 0.46 g (0.99 mmol) of (S,S)-DIPAMP was added as a solid. After 2 minutes stirring a clear orange solution resulted, which was partially stripped. To the residue was then added 10 ml of an solvent A (see table) and the mixture was again partially stripped. A slurry was obtained, which was partially stripped, filtered, and the solid washed with 1/1 mixtures of solvent A and MEK. The products were dried (4 days, 1 mbar, 20° C.) and the composition was analysed by NMR. Isolated yields were above 90%.

| Entry | Solvent A | Content [Rh ((S,S)-DIPAMP)$_2$]BF$_4$ | Solvent content |
|---|---|---|---|
| 1 | Diethyl ether | 0% | 0.5 eq each of diethyl ether and MEK |
| 2 | MTBE | 0% | 0.2 eq MTBE |

The products were recrystallised from methanol yielding complex [Rh cod(S,S)-DIPAMP]BF$_4$.

Example 3

3.09 g (9.95 mmol) of Rh(COD)(acac) was mixed with 60 ml of MEK in a 0.2 litre Schlenk flask. To the resulting clear solution was added 1.4 ml of neat 54% wt tetrafluoroboric acid in diethylether (10.1 mmol) by syringe over a period of 5 minutes, resulting in a red solution. After 10 minutes, 1.35 ml (11.15 mmol) of 1,5-cyclooctadiene was added by syringe. The brown red slurry of Rh(COD)$_2$BF$_4$ was stirred for 30 minutes. Then 4.56 g (9.95 mmol) of (S,S)-DIPAMP was added in 3 portions as a solid. A clear red solution resulted. The stirred solution was then reduced by evaporating MEK solvent until a slurry of the cationic complex in about 10 ml of residual solvent was obtained. To this slurry was added 50 ml of methanol and 45 ml of methanol/MEK was evaporated. The remaining thick slurry was stirred at room temperature for 1 hour before being filtered and washed with 3×10 ml of cold methanol. After drying overnight (1 mbar, 20° C.), 5.3 g of complex [Rh cod(S,S)-DIPAMP]BF$_4$ was obtained. Yield=70.1% (7.01 mmol).

The combined MEK/methanol solutions were partially stripped to a volume of approx 10 ml and 10 ml of 1,4-dioxane was added. From the resulting slurry 10 ml of 1,4-dioxane and methanol mixture was evaporated and the remaining thick slurry was stirred at room temperature for 1 hour before being filtered and washed with 2×5 ml of cold methanol. After drying overnight (1 mbar, 20° C.), 1.7 g of complex [Rh cod(S,S)-DIPAMP]BF$_4$ crystallising with 0.75 mol of dioxane was obtained. Yield=22.5% (2.25 mmol). 3.5% of the impurity [Rh((S,S)-DIPAMP)$_2$]BF$_4$ were found in this second fraction—the reaction formed a total of less than 1% of this impurity. The complex can be used in catalytic applications as obtained.

Example 4

0.25 g (0.809 mmol) of Rh(COD)(acac) was mixed with 5 ml of MEK in a small Schlenk flask. To the resulting clear solution was added 0.12 ml of neat 54% wt tetrafluoroboric acid in diethylether (0.82 mmol) by syringe over a period of 5 minutes, resulting in a red solution.

In a first experiment, 0.05 ml (0.42 mmol) of 1,5-cyclooctadiene was added after 5 minutes. Then the sub-stoichiometric amount of 0.31 g of DPPE (0.75 mmol) was added giving a red solution. This solution was reduced to approx 3 ml and diethyl ether was added precipitating the [Rh cod DPPE]BF$_4$ complex without a contamination by [Rh(DPPE)$_2$]BF$_4$. By $^1$H NMR this compound contained 5 mol % of [Rh(cod)$_2$]BF$_4$.

In a second experiment, 0.2 ml (1.66 mmol) of cis-cyclooctene was added after 5 minutes. Then the sub-stoichiometric amount of 0.31 g of DPPE (0.75 mmol) was added giving a red solution. This solution was reduced to approx 3 ml and diethyl ether was added precipitating the [Rh cod DPPE]BF$_4$ complex without a contamination by [Rh(DPPE)$_2$]BF$_4$.

The products of the two experiments were dissolved in 10 ml of acetone, purged with nitrogen and the solution treated with hydrogen (5 bar) for 2 hours. The brown slurry was filtered, and the light brown solid was washed with acetone until the acetone wash solution was colourless. After drying 0.36 g of [Rh DPPE]$_2$ (BF$_4$)$_2$ (0.306 mmol, 82% yield calculated from amount of DPPE) was obtained as an light brown product. The combined acetone solutions were stripped and by NMR analysis shown to contain no remaining [Rh cod DPPE]BF$_4$, but compounds that are likely to contain [Rh (acetone)$_x$ DPPE]BF$_4$.

Example 5

3.09 g (9.95 mmol) of Rh(COD)(acac) was mixed with 60 ml of MEK in a 0.2 litre Schlenk flask. To the resulting clear solution was added 1.4 ml of neat 54% wt tetrafluoroboric acid in diethylether (10.1 mmol) by syringe over a period of 5 minutes, resulting in a red solution. After 10 minutes, 1.35 ml (11.15 mmol) of 1,5-cyclooctadiene was added by syringe. The brown red slurry of Rh(COD)$_2$BF$_4$ was stirred for 30 minutes. Then 2.63 g of triphenylphosphine (9.95 mmol) was added in 1 portion. A clear red solution resulted. Upon addition of a second amount of 2.63 g of triphenylphosphine (9.95 mmol) an orange slurry was obtained. The slurry was then reduced by evaporating MEK solvent until a slurry of the cationic complex in about 10 ml of residual solvent was obtained. To this slurry was added 30 ml of ethanol and 45 ml of ethanol/MEK was evaporated. The remaining thick slurry was stirred at room temperature for 1 hour before being filtered and washed with 3×10 ml of cold ethanol. After drying overnight (1 mbar, 20° C.), 7.65 g of complex [Rh cod (PPh$_3$)$_2$]BF$_4$ was obtained. Yield=93.5% (9.3 mmol).

Example 6

2.679 g (8.635 mmol) of Rh(COD)(acac) was mixed with 20 ml of MEK in a 0.1 litre Schlenk flask. To the resulting slurry was added by syringe 1.22 ml of neat 54% wt tetrafluoroboric acid in diethylether (8.74 mmol) by syringe over a period of 2 minutes, resulting in a red solution. After 5 minutes, 1.17 ml (9.66 mmol) of 1,5-cyclooctadiene was added by syringe. The brown red slurry was stirred for 20 minutes. Then 4.65 g (8.635 mmol) of DPEPhos was added in 2 portions over a period of 3 minutes. A orange slurry resulted after 5 minutes. The stirred slurry was reduced by evaporating MEK solvent until a slurry of the cationic complex in about 10 ml of residual solvent was obtained. To this slurry was added 20 ml of ethanol. The resulting orange slurry was degassed and stirred at room temperature for 1 hour before being filtered and washed with 2×5 ml of cold ethanol. After drying overnight (1 mbar, 20° C.), gave 7.26 g of complex [Rh cod DPEPhos]BF$_4$ with approximately 0.75 equivalents of ethanol, Yield=98.5% (8.51 mmol).

Example 7

6.18 g (19.9 mmol) of Rh(COD)(acac) was mixed with 160 ml of acetone in a 0.4 litre Schlenk flask. To the resulting slurry was added by syringe 2.62 ml of 48% aqueous tetrafluoroboric acid (20.2 mmol) over a period of 5 minutes, resulting in a red solution. After 10 minutes, 2.7 ml (22.3 mmol) of 1,5-cyclooctadiene was added by syringe. The red solution was stirred for 60 minutes and then heated to about 50° C. Then 11.5 g (19.9 mmol) of (S)-PHANEPHOS was added in 3 portions as a solid. A clear red solution resulted. The stirred solution was then heated to about 50° C. for one hour and then reduced by evaporating acetone solvent. To a residual 20 ml of red syrupy solution with some red crystals was added 80 ml of iso-propanol. The resulting slurry was degassed and heated to about 70° C. for 1 hour. Then about 80 ml of iso-propanol/acetone solvent was evaporated. The remaining thick slurry was stirred at room temperature for 1 hour before being filtered and washed with 2×10 ml of cold iso-propanol. After drying over a weekend (1 mbar, 20° C.), 16.1 g of complex [Rh cod(S)-PHANEPHOS]$BF_4$ with approximately 0.6% wt residual iso-propanol and 0.1% wt of residual acetone was obtained. Corrected yield=92.0% (18.30 mmol).

This complex can be used in catalytic applications as obtained or further dried at 50° C., 4 mbar to remove more of the residual solvent.

The complex [Rh cod(S)-PHANEPHOS]$BF_4$ with approximately 0.6% wt residual iso-propanol and 0.1% wt of residual acetone was dissolved in dichloromethane and the solvent was partially stripped. Most of the residual iso-propanol and acetone can be removed using this procedure.

An NMR experiment was also performed to show the formation of the desired complex takes place in the ketone solvent. To 30.9 mg of Rh(COD)(acac) in 0.4 ml of $d^6$ acetone 0.02 ml of 54% wt tetrafluoroboric acid in diethylether was added followed by addition of 0.1 ml of 1,5-cyclooctadiene. The mixture was shaken and heated to about 50° C. After a short period, 57.5 mg of (S)-PHANEPHOS was added the mixture was heated to about 50° C. for a short time. A $^{31}P\{^1H\}$ NMR spectrum obtained on this showed the complex [Rh cod(S)-PHANEPHOS]$BF_4$ had formed.

Example 8

6.18 g (19.9 mmol) of Rh(COD)(acac) was mixed with 140 ml of MEK in a 0.4 litre Schlenk flask. To the resulting slurry was added by syringe 2.62 ml of 48% aqueous tetrafluoroboric acid (20.2 mmol) over a period of 5 minutes, resulting in a red solution. After 10 minutes, 1.35 ml (11.15 mmol) of 1,5-cyclooctadiene was added by syringe. The brown red slurry was stirred for 20 minutes and then heated to about 30° C. Then 12.38 g (19.9 mmol) of (rac)-BINAP was added in 4 portions over a period of 5 minutes. A clear red solution resulted. The stirred solution was then heated to about 50° C. for one hour and then reduced by evaporating MEK solvent, which caused crystallisation to occur. Removal of the ketone solvent was continued until a slurry of the cationic complex in about 25 ml of residual solvent was obtained. To this slurry was added 50 ml of ethanol. The resulting orange slurry was degassed and heated to about 70° C. for 1 hour, before evaporating off about 60 ml of ethanol/MEK. The remaining thick slurry was stirred at room temperature for 1 hour before being filtered and washed with 2×15 ml of cold ethanol. After drying overnight (1 mbar, 20° C.), gave 16.56 g of complex [Rh cod (rac)-BINAP]$BF_4$, crystallising with 0.5 mol of ethanol Yield=90.7% (18.04 mmol).

Example 9

7.43 g (23.9 mmol) of Rh(COD)(acac) was mixed with 140 ml of MEK in a 0.4 litre Schlenk flask. To the resulting slurry was added by syringe 3.15 ml of 48% aqueous tetrafluoroboric acid (24.3 mmol) over a period of 5 minutes, resulting in a red solution. After 10 minutes, 1.35 ml (11.15 mmol) of 1,5-cyclooctadiene was added by syringe. The brown red slurry was stirred for 20 minutes and then heated to about 30° C. Then 10.0 g (23.9 mmol) of 1,1'-bis-(diisopropylphosphino)ferrocene (DIPFC) was added in 4 portions over a period of 5 minutes. A clear red solution resulted. The stirred solution was then heated to about 50° C. for one hour and then reduced by evaporating MEK solvent until a slurry of the cationic complex in about 25 ml of residual solvent was obtained. To this slurry was added 50 ml of ethanol. The resulting orange slurry was degassed and heated to about 70° C. for 1 hour, before evaporating off about 60 ml of ethanol/MEK. The remaining thick slurry was stirred at room temperature for 1 hour before being filtered and washed with 2×15 ml of cold ethanol. After drying overnight (1 mbar, 20° C.), gave 15.2 g of complex [Rh cod DIPFC]$BF_4$, Yield=91% (21.75 mmol).

Example 10

537 mg (1.73 mmol) of Rh(COD)(acac) was mixed with 10 ml of MEK in a small Schlenk flask. To the resulting slurry was added by syringe 0.23 ml of 48% aqueous tetrafluoroboric acid (1.76 mmol) over a period of 2 minutes, resulting in a red solution. After 10 minutes, 0.1 ml (0.83 mmol) of 1,5-cyclooctadiene was added by syringe. The brown red slurry was stirred for 20 minutes and then 1 g of 1,1'-bis-(dicyclohexylphosphino)ferrocene (DCyPFC) (1.73 mmol) was added. A clear red solution resulted. The stirred solution was then reduced by evaporating MEK solvent. Removal of the ketone solvent was continued until a slurry of the cationic complex in about 3 ml of residual solvent was obtained. To this slurry was added 3 ml of ethanol. The resulting orange slurry was degassed and stripped to about 4 ml of ethanol/MEK. The remaining thick slurry was stirred at room temperature for 1 hour before being filtered and washed with 2×2 ml of cold ethanol. After drying overnight (1 mbar, 20° C.), gave 1.44 g of complex [Rh cod DCyPFC]$BF_4$, Yield=95.4% (1.65 mmol).

Example 11

3.09 g (9.95 mmol) of Rh(COD)(acac) was mixed with 80 ml of MEK in a 0.2 litre Schlenk flask. To the resulting clear solution was added 1.4 ml of neat 54% wt tetrafluoroboric acid in diethylether (10.1 mmol) by syringe over a period of 5 minutes, resulting in a red solution. After 10 minutes, 1.35 ml (11.15 mmol) of 1,5-cyclooctadiene was added by syringe. The brown red slurry of Rh(COD)$_2$$BF_4$ was stirred for 60 minutes and then heated to about 50° C. Then 6.62 g (9.95 mmol) of (S)-PPHOS was added in 3 portions as a solid. A clear red solution resulted. The stirred solution was then heated to about 50° C. for one hour and then reduced by evaporating MEK solvent, which caused crystallisation to occur. Removal of the ketone solvent was continued until a slurry of the cationic complex in about 10 ml of residual solvent was obtained. To this slurry was added 50 ml of iso-propanol. The resulting orange slurry was degassed and heated to about 70° C. for 1 hour, before evaporating off about 45 ml of iso-propanol/MEK. The remaining thick slurry was stirred at room temperature for 1 hour before being filtered and washed with 2×10 ml of cold iso-propanol. After drying overnight (1 mbar, 20° C.), gave 8.7 g of complex [Rh cod (S)-PPHOS]$BF_4$ with approximately 0.3% wt residual iso-propanol. Yield=92.6% (9.21 mmol).

This complex can be used in catalytic applications as obtained or further dried at 50° C., 1 mbar to remove more of the residual solvent.

Example 12

1.03 g (3.32 mmol) of Rh(COD)(acac) was mixed with 20 ml of MEK in a 0.2 litre Schlenk flask. To the resulting clear solution was added 0.47 ml of neat 54% wt tetrafluoroboric acid in diethylether (3.36 mmol) by syringe over a period of 5 minutes, resulting in a red solution. After 10 minutes, 0.2 ml (1.66 mmol) of 1,5-cyclooctadiene was added by syringe giving a brown red slurry. Then 2.21 g (3.32 mmol) of (S)-PPHOS was added as a solid. A clear red solution resulted. The stirred solution was heated to about 50° C. and then reduced by evaporating MEK solvent, which caused crystallisation to occur. Removal of the ketone solvent was continued until a slurry of the cationic complex in about 10 ml of residual solvent was obtained. To this slurry was added 20 ml of iso-propanol. The resulting orange slurry was degassed and about 30 ml of iso-propanol/MEK was evaporated. The remaining thick slurry was stirred at room temperature for 1 hour before being filtered and washed with 2×5 ml of cold iso-propanol. After drying overnight (1 mbar, 20° C.), gave 2.85 g of complex [Rh cod(S)-PPHOS]$BF_4$ of a purity similar to Example 11. Yield=90.6% (3.02 mmol).

Example 13

1.03 g (3.32 mmol) of Rh(COD)(acac) was mixed with 20 ml of MEK in a 0.2 litre Schlenk flask. To the resulting clear solution was added 0.47 ml of neat 54% wt tetrafluoroboric acid in diethylether (3.36 mmol) by syringe over a period of 5 minutes, resulting in a red solution. After 10 minutes, 0.8 ml (6.65 mmol) of cis-cyclooctene was added by syringe giving a red solution. Then 2.21 g (3.32 mmol) of (S)-PPHOS was added as a solid. A clear red solution resulted. The stirred solution was heated to about 50° C. and then reduced by evaporating MEK solvent, which caused crystallisation to occur. Removal of the ketone solvent was continued until a slurry of the cationic complex in about 10 ml of residual solvent was obtained. To this slurry was added 20 ml of iso-propanol. The resulting orange slurry was degassed and about 30 ml of iso-propanol/MEK was evaporated. The remaining thick slurry was stirred at room temperature for 1 hour before being filtered and washed with 2×5 ml of cold iso-propanol. After drying overnight (1 mbar, 20° C.), gave 2.85 g of complex [Rh cod(S)-PPHOS]$BF_4$ of a purity similar to Example 11. Yield=90.6% (3.02 mmol).

Example 14

0.465 g (1.5 mmol) of Rh(COD)(acac) was mixed with 9 ml of MEK in a 0.2 litre Schlenk flask. To the resulting clear solution was added 0.21 ml of neat 54% wt tetrafluoroboric acid in diethylether (1.52 mmol) by syringe over a period of 2 minutes, resulting in a red solution. After 5 minutes, 0.09 ml (0.75 mmol) of 1,5-cyclooctadiene was added by syringe giving a brown red slurry. Then 1.135 g (1.5 mmol) of (R)-Xyl PPHOS was added as a solid. A clear red solution resulted. After 3 hours the stirred solution was reduced by evaporating MEK solvent until a slurry of the cationic complex in some residual solvent was obtained. To this slurry was added 15 ml of heptane and the product was filtered, washed with heptane and dried for 15 hours (20° C., 1 mbar). Crude [Rh cod (R)-Xyl PPHOS]$BF_4$ containing no [Rh(R)-Xyl PPHOS]$BF_4$ was obtained. This product was slurried in diethyl ether and stirred for 3 hours. The thick slurry was filtered and washed with 2×10 ml of cold diethyl ether. Drying 15 hours (1 mbar, 20° C.), gave 1.26 g of the [Rh cod (R)-Xyl PPHOS]$BF_4$ complex containing close to 0.25 molar equivalents of MEK, that is retained during further drying. The dried product contains less than 1 mol % of [Rh(R)-Xyl PPHOS]$BF_4$. Yield=79.6% (1.20 mmol). This complex can be used in catalytic applications as obtained.

Example 15

0.465 g (1.5 mmol) of Rh(COD)(acac) was mixed with 9 ml of MEK in a 0.2 litre Schlenk flask. To the resulting clear solution was added 0.21 ml of neat 54% wt tetrafluoroboric acid in diethylether (1.52 mmol) by syringe over a period of 2 minutes, resulting in a red solution. After 5 minutes, 0.09 ml (0.75 mmol) of 1,5-cyclooctadiene was added by syringe giving a brown red slurry. Then 1.135 g (1.5 mmol) of (R)-Xyl PPHOS was added as a solid. A clear red solution resulted. After 3 hours the stirred solution was reduced by evaporating MEK solvent until a slurry of the cationic complex in some residual solvent was obtained. To this slurry was added 15 ml of heptane and the product was filtered, washed with heptane and dried for 15 hours (20° C., 1 mbar). Crude [Rh cod (R)-Xyl PPHOS]$BF_4$ containing no [Rh(R)-Xyl PPHOS]$BF_4$ was obtained. This product was slurried in MTBE and stirred for 3 hours. The thick slurry was filtered and washed with 2×10 ml of cold MTBE. Drying 15 hours (1 mbar, 20° C.), gave 1.27 g of the [Rh cod (R)-Xyl PPHOS]$BF_4$ complex containing close to 0.75 molar equivalents of MTBE, that is retained during further drying. The dried product contains no [Rh(R)-Xyl PPHOS]$BF_4$, Yield=79.6% (1.20 mmol). This complex can be used in catalytic applications as obtained.

Example 16

2.154 g (6.95 mmol) of Rh(COD)(acac) was mixed with 42 ml of MEK in a 0.2 litre Schlenk flask. To the resulting clear solution was added 0.97 ml of neat 54% wt tetrafluoroboric acid in diethylether (7.04 mmol) by syringe over a period of 5 minutes, resulting in a red solution. After 5 minutes, 0.42 ml (3.47 mmol) of 1,5-cyclooctadiene was added by syringe giving a brown red slurry. Then 5.26 g (6.95 mmol) of (R)-Xyl PPHOS was added in 3 portions as a solid. A clear red solution resulted. After 3 hours the stirred solution was reduced by evaporating MEK solvent until a slurry of the cationic complex in some residual solvent was obtained. To this slurry was added 50 ml of heptane and the product was filtered, washed with heptane and 2×5 ml of diethyl ether and dried for 15 hours (20° C., 1 mbar). Crude [Rh cod (R)-Xyl PPHOS]$BF_4$ containing no [Rh(R)-Xyl PPHOS]$BF_4$ was obtained. This product was slurried in MTBE and stirred for 3 hours. The thick slurry was filtered and washed with 2×20 ml of cold MTBE. Drying 4 days (1 mbar, 20° C.), gave 6.1 g of the [Rh cod (R)-Xyl PPHOS]$BF_4$ complex containing close to 0.33 molar equivalents of MTBE, that is retained during further drying. The dried product contains less than 1 mol % of [Rh(R)-Xyl PPHOS]$BF_4$. Yield=83.6% (5.81 mmol). This complex can be used in catalytic applications as obtained.

Example 17

0.309 g (0.995 mmol) of Rh(COD)(acac) was mixed with 8 ml of MEK in a small Schienk flask. To the resulting clear solution was added 0.14 ml of neat 54% wt tetrafluoroboric acid in diethylether (1.02 mmol) by syringe over a period of 2 minutes, resulting in a red solution. After 5 minutes, 0.05 ml (0.42 mmol) of 1,5-cyclooctadiene was added by syringe giving a brown red slurry. The slurry was cooled in an ice bath.

0.4 g of an oil containing by $^{31}$P NMR integration 67% of rac-TCFP had been prepared with hexachlorodisilane according to US2005/228190 (Example 21). This impure oil was dissolved in 4 ml of MEK and the solution was cooled in the ice bath and added to the slurry of the Rh compound. A further 4 ml were required to rinse the ligand flask. A clear solution resulted which was partially stripped to approx 3 ml and analysed by $^{31}$P NMR as containing rac-[Rh cod TCFP]BF$_4$ contaminated with 20% of other Rh phosphine compounds.

At this point 8 ml of 2-propanol were added and the mixture was stirred for 15 minutes and then partially stripped to obtain a slurry. A first crop of 0.3 g of pure rac-[Rh cod TCFP]BF$_4$ (0.54 mmol, 54% yield calculated from Rh cod acac used) containing no [Rh cod$_2$]BF$_4$ was obtained. A second crop contained 0.1 g of rac-[Rh cod TCFP]BF$_4$ contaminated with 2% of [Rh cod$_2$]BF$_4$. The stripped mother liquor contained some remaining [Rh cod$_2$]BF$_4$. Combined yield 0.71 mmol, 71% yield calculated from [Rh cod acac] used).

Example 18

With a remaining quantity of 0.16 g of the oil containing by $^{31}$P NMR integration 67% of rac-TCFP used in Example 17 the synthesis of rac-[Rh cod TCFP] trifluoromethansulfonate was attempted: 0.124 g (0.4 mmol) of Rh(COD)(acac) was mixed with 4 ml of MEK in a small Schlenk flask. To the resulting clear solution was added 0.04 ml of neat trifluoromethanesulfonic acid (0.4 mmol) by syringe over a period of 2 minutes, resulting in a red solution. After 5 minutes, 0.05 ml (0.42 mmol) of 1,5-cyclooctadiene was added by syringe giving a brown orange solution. The slurry was cooled in an ice bath and the solution of the ligand was added and the complex isolated as in Example 17. A solid product (80 mg) containing by NMR 9% of [Rh cod$_2$] trifluoromethansulfonate was obtained. This was again recrystallised from methanol/diethylether and gave pure rac-[Rh cod TCFP] trifluoromethansulfonate.

Example 19

3.3 g of the impure ligand (S)-TCFP was prepared from 8.8 g of intermediate 29 in US2005/228190. As estimated by analysing the $^{31}$P NMR spectrum a mixture containing 2.83 g of (S)-TCFP (10.8 mmol) and 0.47 g of partially desulfurised compound A (1.6 mmol) was obtained.

3.60 g (11.6 mmol) of Rh(COD)(acac) was mixed with 80 ml of MEK in a 0.2 litre Schlenk flask. To the resulting clear solution was added 1.63 ml of neat 54% wt tetrafluoroboric acid in diethylether (11.78 mmol) by syringe over a period of 5 minutes, resulting in a red solution. After 10 minutes, 1.35 ml (11.15 mmol) of 1,5-cyclooctadiene was added by syringe. The brown red slurry was stirred for 10 minutes and the cooled to 0° C. in an ice bath. The impure ligand (S)-TCFP as described above was dissolved in 10 ml of MEK and the solution was added dropwise to the brown red slurry of Rh(COD)$_2$BF$_4$. A clear red solution resulted upon completion of addition and $^{31}$P NMR confirmed consumption of all phosphines forming a mixture of 95 mol % of (S)-[Rh cod TCFP]BF$_4$ and 5 mol % of a [Rh cod (A)$_2$]BF$_4$ compound. The solution was then reduced by evaporating MEK solvent, which caused crystallisation to occur. To a slurry containing about 10 ml of residual MEK solvent was added 30 ml of iso-propanol and 30 ml of iso-propanol/MEK were stripped. The remaining thick slurry was stirred at room temperature for 1 hour before being filtered and washed with 2×10 ml of cold iso-propanol. After drying overnight (1 mbar, 20° C.) 5.8 g of complex (S)-[Rh cod TCFP]BF$_4$ (10.35 mmol, 95% recovery of (S)-TCFP content) was obtained. The mother liquor contained a mixture of 50 mol % of (S)-[Rh cod TCFP] BF$_4$ and [Rh cod (A)$_2$]BF$_4$.

Example 20

3.09 g (9.95 mmol) of Rh(COD)(acac) was mixed with 80 ml of MEK in a 0.2 litre Schlenk flask. To the resulting clear solution was added 0.895 ml of neat trifluoromethanesulfonic acid (10.1 mmol) diluted with 10 ml of MEK was added by syringe over a period of 5 minutes. After 10 minutes, 1.35 ml (11.15 mmol) of 1,5-cyclooctadiene was added by syringe. The brown orange solution of Rh(COD)$_2$ trifluoromethanesulfonate was stirred for 60 minutes and then heated to about 50° C. 6.12 g (9.95 mmol) of (R)-Me Bophoz was added in portions as a solid resulting in a red solution. The stirred solution was then heated to about 50° C. for one hour and then reduced by evaporating MEK solvent until a syrupy solution of the cationic complex in about 10 ml of residual MEK was obtained. To this solution was added 80 ml of ethanol and the solvent mixture was again stripped until a thick slurry of product in about 15 ml of residual solvent was obtained. The slurry was stirred at room temperature for 1 hour before being filtered and washed with 2×10 ml of cold iso-propanol. Drying 15 hours at 20° C. gave 8.05 g of the [Rh cod (R)-Me Bophoz] trifluoromethanesulfonate complex, containing some retained ethanol. Yield 82.4% (8.2 mmol).

Example 21

3.09 g (9.95 mmol) of Rh(COD)(acac) was mixed with 80 ml of MEK in a 0.2 litre Schlenk flask. To the resulting clear solution was added 1.4 ml of neat 54% wt tetrafluoroboric acid in diethylether (10.1 mmol) by syringe over a period of 5 minutes, resulting in a red solution. After 10 minutes, 1.35 ml (11.15 mmol) of 1,5-cyclooctadiene was added by syringe. The brown red slurry of Rh(COD)$_2$BF$_4$ was stirred for 60 minutes and then heated to about 50° C. Then 6.63 g (9.95 mmol) of (S)—H$^8$BinamP was added in 3 portions as a solid. A clear red solution resulted. The stirred solution was then heated to about 50° C. for one hour and then reduced by evaporating MEK solvent, which caused crystallisation to occur. Removal of the ketone solvent was continued until a slurry of the cationic complex in about 10 ml of residual solvent was obtained. To this slurry was added 50 ml of iso-propanol. The resulting orange slurry was degassed and heated to about 70° C. for 1 hour, before evaporating off about 45 ml of iso-propanol/MEK. The remaining thick slurry was stirred at room temperature for 1 hour before being filtered and washed with 2×10 ml of cold iso-propanol. After drying overnight (1 mbar, 20° C.), gave 4.7 g of complex [Rh cod (S)—H$^8$BinamP]BF$_4$ with one mol of coordinated iso-propanol. Yield=49.2% (4.90 mmol). This complex can be used in catalytic applications as obtained.

Upon addition of 50 ml of MTBE to the isopropanol mother liquors, a further 3.2 g of complex containing MTBE was obtained.

Example 22

An autoclave glass inlet was charged with 0.25 g (0.809 mmol) of Rh(COD)(acac) and 10 ml of acetone. The solution was saturated with argon and 0.12 ml of neat 54% wt tetrafluoroboric acid in diethylether (0.82 mmol) was added by syringe over a period of 2 minutes. After 5 minutes, 0.05 ml (0.42 mmol) of 1,5-cyclooctadiene was added. Then, the amount of 0.325 g of DPPE (0.815 mmol) was added giving after stirring a red solution. This solution was saturated with argon and analysed by $^{31}$P NMR and found to contain [Rh cod DPPE]BF$_4$, contaminated with less than 3% of [Rh(DPPE)$_2$] BF$_4$.

The glass inlet was placed in a Parr vessel and the solution was purged with nitrogen. The solution was then treated with hydrogen (5 bar) for 2 hours. The yellow slurry was filtered, and the yellow solid was washed with acetone until the acetone wash solution was colourless. After drying 0.37 g of [Rh DPPE]$_2$ (BF$_4$)$_2$ (0.32 mmol, 80% yield) was obtained as a bright yellow product.

| Experiment | Ligand | Quantity | L/Rh | Conversion (%) |
|---|---|---|---|---|
| 1 | (Sa,Rc)-(1-Nph)-Quinaphos | 14.8 mg | 2.25 | >80 |
| 2 | Mixture Triphenylphosphine and (S)-Monophos [185449-86-9] | 2.6 mg and 3.6 mg | 1.1 and 1.05 | >60 |
| 3 | (S)-Monophos [185449-86-9] | 7.2 mg | 2.1 | >40 |
| 4 | Selke Ph-β-GLUP | 7.12 mg | 1.1 | >80 |

The combined acetone solutions were stripped and by NMR analysis shown to contain a smaller amount of remaining [Rh cod DPPE]BF$_4$.

Example 23

An autoclave glass inlet was charged with 0.618 g (1.99 mmol) of Rh(COD)(acac) and 10 ml of acetone. The slurry was saturated with argon and 0.28 ml of neat 54% wt tetrafluoroboric acid in diethylether (0.82 mmol) was added by syringe over a period of 2 minutes. After 5 minutes, 0.124 ml (1.03 mmol) of 1,5-cyclooctadiene was added. Then, 0.798 g of DPPE (2.00 mmol) was added giving a red solution on stirring. This solution was saturated with argon and analysed by $^{31}$P NMR and found to contain [Rh cod DPPE]BF$_4$ contaminated with less than 2% of [Rh(DPPE)$_2$]BF$_4$.

The glass inlet was placed in a Parr vessel and the solution was purged with nitrogen. The solution was then treated with hydrogen (5 bar) for 3 hours. The yellow slurry was filtered, and the yellow solid was washed with acetone until the acetone wash solution was colourless. After drying 0.940 g of [Rh DPPE]$_2$ (BF$_4$)$_2$ (0.81 mmol, 81% yield) was obtained as a yellow product.

Example 24

The Example 23 was repeated with the only change that 0.28 ml of neat 54% wt tetrafluoroboric acid in diethylether (0.82 mmol) was replaced by 0.179 ml of trifluoromethanesulfonic acid. Before the hydrogenation, a clear yellow solution of [Rh cod DPPE] trifluoromethanesulfonate, contaminated with less than 1% of [Rh(DPPE)$_2$] trifluoromethanesulfonate was obtained.

Example 25

27 mg (71 micromol) of Rh(NBD)(acac) was mixed with 4 ml of acetone in a small Schlenk flask. To the resulting clear solution was added 0.11 ml of a stock solution prepared by adding 0.1 ml of neat 54% wt tetrafluoroboric acid in diethylether to 1 ml of acetone (1.02 eq), resulting in a red solution. After 1 minute, 20 microlitre (1 eq) of norbornadiene was added by syringe. 0.5 ml aliquots containing 9 micromoles of cationic Rh-complex was added to ligand samples as detailed in the table. Clear yellow to red solutions were obtained and aliquots were analysed by $^{31}$P NMR adding some d$^6$ acetone. $^{31}$P NMR showed a virtually complete consumption of the ligand and formation of cationic Rh-complexes.

4 samples of 0.32 g of α-methylcinnamic acid were weighed into 4 glass liners of the Biotage Endeavour screening unit and to each was added 4 ml of acetone. After the addition of the catalyst solutions, the acetone solutions were purged several times with nitrogen. Hydrogenation at a substrate to catalyst ratio 200/1 was carried out at 25° C. and 15 bar for 60 hours, giving conversions as indicated in the table.

Example 26

1.54 g (4.975 mmol) of Rh(COD)(acac) was mixed with 30 ml of MEK in a 0.2 litre Schlenk flask. To the resulting slurry was added 0.75 ml of neat 54% wt tetrafluoroboric acid in diethylether (5.05 mmol) by syringe over a period of 5 minutes, resulting in a red solution. After 10 minutes, 0.14 ml (1.2 mmol) of 1,5-cyclooctadiene was added by syringe followed by the addition of 6.19 g (9.95 mmol) of (S)-BINAP in one portion. After 15 minutes the resulting slurry was diluted with 14 ml of MEK and split into 3 aliquots of 20 ml of solution. Under nitrogen each aliquot was transferred into an autoclave glass inlet in a Parr autoclave and hydrogenated at 21 bar of hydrogen, 25° C. for 15 hours. The hydrogen uptake ceased within 15 minutes of pressurising the autoclave with hydrogen. After venting the hydrogen the contents of the autoclave (red slurry) were transferred into a Schlenk flask and the glass inlet was rinsed with further MEK. Upon partial removal of the MEK solvent a thick slurry was obtained. After all 3 hydrogenation batches were combined in the same Schlenk flask the concentrated slurry was filtered and the product was washed with 2×10 ml of MEK. A first crop of 5.05 g of [Rh{(S)-Binap}$_2$]BF$_4$ was isolated. From the mother liquor a further 0.45 g of [Rh{(S)-Binap}$_2$]BF$_4$ were obtained. Isolated yield 77% based on Rh(COD)(acac) used.

The invention claimed is:

1. A process for the synthesis of a cationic [rhodium diolefin phosphorus ligand] complex comprising the steps of:
   (a) reacting a rhodium-diolefin-1,3-diketonate and an acid in a ketone solvent,
   (b) adding a stabilising olefin to form a stabilised cationic rhodium compound, and
   (c) mixing a phosphorus ligand with the solution of the stabilised cationic rhodium compound to form a solution of the cationic [rhodium diolefin phosphorus ligand] complex.

2. The process according to claim 1, wherein the rhodium-diolefin-1,3-diketonate is Rh(COD)(1,3-diketonate) or Rh(NBD)(1,3-diketonate), wherein the 1,3-diketonate is selected from the group consisting of acetylacetonate, hexafluoroacetylacetonate and 1,5-dimethylacetylacetonate.

3. The process according to claim 1, wherein the ketone solvent has a boiling point below 160° C. at atmospheric pressure.

4. The process according to claim 1, wherein the ketone solvent is selected from the group consisting of acetone, methyl-ethyl ketone (MEK), methyl-isobutyl ketone (MIBK) and diethylketone.

5. The process according to claim 1, wherein the ketone solvent is methyl-ethyl ketone (MEK) or acetone.

6. The process according to claim 1, wherein the acid is a perfluorinated acid.

7. The process according to claim 1, wherein the acid is selected from the group consisting of tetrafluoroboric acid ($HBF_4$), trifluoromethanesulfonic acid ($CF_3SO_3H$), hexafluorophosphoric acid ($HPF_6$), hexafluoroantimonic acid ($HSbF_6$) and perfluoro alkylsulfonic acids.

8. The process according to claim 1, wherein the stabilising olefin is a cyclic monoolefin.

9. The process according to claim 1, wherein the stabilising olefin is cyclooctene.

10. The process according to claim 1, wherein the stabilising olefin is a cyclic diolefin and is the same as that present in the rhodium-diolefin-1,3-diketonate.

11. The process according to claim 1, wherein the phosphorus ligand is a chiral or achiral, monodentate or bidentate phosphorus ligand in which each phosphorus atom is covalently bonded to 3 carbon atoms, or covalently bonded to n heteroatoms and 3-n carbon atoms, where n=1, 2 or 3.

12. The process according to claim 11, wherein the phosphorus atom is covalently bonded to said n heteroatoms and each of said heteroatoms is selected from the group consisting of N and O.

13. The process according to claim 1, wherein the phosphorus ligand is selected from the group consisting of substituted or unsubstituted $PPh_3$, Binap, Bis[(2-diphenylphosphino)phenyl]ether, PPhos ligands, Phanephos, Bophoz ligands, BinamP, $H^8$-BinamP, Quinaphos, Selke ligands, DIPAMP, 1,2-Bis(diphenylphosphino)ethane, TCFP, Dihydroquinaphos, Monophos ligands, DIPFC and DCyPFC.

14. The process according to claim 1, further comprising:
(i) evaporating at least a portion of the ketone solvent from the solution obtained in step (c) to form a slurry or a concentrated solution of the cationic [rhodium diolefin phosphorus ligand] complex,
(ii) optionally treating the resulting solution of the complex with an anti-solvent selected from the group consisting of low boiling ethers and alkanes to precipitate the complex,
(iii) recovering the cationic [rhodium diolefin phosphorus ligand] complex as a solid, and
(iv) optionally slurrying the solid cationic [rhodium diolefin phosphorus ligand] complex in an anti-solvent selected from the group consisting of low boiling ethers and alkanes and repeating step (iii).

15. The process according to claim 14, wherein the anti-solvent is selected from the group consisting of dialkyl ethers, pentane isomers, hexane isomers, heptane isomers, octane isomers, 5-membered cycloalkyl ethers and 6-membered cycloalkyl ethers.

16. The process according to claim 14, further comprising:
(a') forming a solution of the cationic [rhodium diolefin phosphorus ligand] complex in a ketone solvent,
(b') hydrogenating the solution of the cationic [rhodium diolefin phosphorus ligand] complex, and
(c') recovering a cationic [rhodium phosphorus ligand]$_2$ complex as a solid.

17. The process according to claim 14, further comprising:
(a') forming a solution of the cationic [rhodium diolefin phosphorus ligand] complex in a ketone solvent,
(b') adding an arene or a phosphorus ligand to the solution of the cationic [rhodium diolefin phosphorus ligand] complex,
(c') hydrogenating the mixture of step (b'), and
(d') recovering as a solid a cationic [rhodium arene phosphorus ligand] complex or a cationic [rhodium (phosphorus ligand)$_2$] complex.

18. The process according to claim 1, further comprising:
(i) optionally evaporating at least a portion of the ketone solvent from the solution obtained in step (c) to form a slurry or a concentrated solution of the cationic [rhodium diolefin phosphorus ligand] complex,
(ii) adding to the solution obtained in step (c), or to the slurry or concentrated solution obtained in (i), a suitable amount of a co-solvent, and
(iii) evaporating at least a portion of the ketone solvent/co-solvent mixture to obtain a modified slurry or modified concentrated solution of the cationic [rhodium diolefin phosphorus ligand] complex.

19. The process according to claim 18, wherein the co-solvent is selected from the group consisting of alcohols, weakly-coordinating ethers, esters, chlorinated hydrocarbons and mixtures thereof.

20. The process according to claim 18, wherein the co-solvent is an alcohol with a boiling point at atmospheric pressure below 165° C.

21. The process according to claim 18, wherein the co-solvent is selected from the group consisting of methanol, ethanol, 2-propanol, 1-butanol, 2-butanol, 3-methyl-2-butanol, 2-methyl-2-butanol and 3-methyl-1-butanol.

22. The process according to claim 18, wherein the co-solvent is an alcohol with a higher boiling point than the ketone solvent and the amount of alcohol is ≥2:1 by volume of the ketone solvent in the slurry or concentrated solution of the rhodium complex.

23. The process according to claim 18, further comprising:
(iv) crystallising at least one crop of the complex from the modified slurry or modified concentrated solution at a temperature between −40° C. and 100° C., and
(v) recovering the cationic [rhodium diolefin phosphorus ligand] complex as a solid.

24. The process according to claim 23, further comprising:
(vi) treating the solid cationic [rhodium diolefin phosphorus ligand] complex with a co-solvent, anti-solvent or mixture thereof, wherein the co-solvent may be the same or different to the co-solvent in step (iv);
(vii) concentrating the product of step (vi); and
(viii) optionally repeating steps (iv) and (v).

25. The process according to claim 18, further comprising:
(a') forming a solution of the cationic [rhodium diolefin phosphorus ligand] complex in a ketone solvent,
(b') hydrogenating the solution of the cationic [rhodium diolefin phosphorus ligand] complex, and
(c') recovering a cationic [rhodium phosphorus ligand]$_2$ complex as a solid.

26. The process according to claim 18, further comprising:
(a') forming a solution of the cationic [rhodium diolefin phosphorus ligand] complex in a ketone solvent,
(b') adding an arene or a phosphorus ligand to the solution of the cationic [rhodium diolefin phosphorus ligand] complex,
(c') hydrogenating the mixture of step (b'), and
(d') recovering as a solid a cationic [rhodium arene phosphorus ligand] complex or a cationic [rhodium (phosphorus ligand)$_2$] complex.

27. The process according to claim 1, further comprising recovering the complex and drying the recovered complex at a temperature in the range 10 to 60° C. under 1 to 30 mbar of pressure for between 1 hour and 5 days.

28. The process according to claim 1, further comprising:
(a') hydrogenating the solution of the cationic [rhodium diolefin phosphorus ligand] complex, and
(b') recovering a cationic [rhodium phosphorus ligand]$_2$ complex as a solid.

29. The process according to claim 1, further comprising:
(a') adding an arene or a phosphorus ligand to the solution of the cationic [rhodium diolefin phosphorus ligand] complex,
(b') hydrogenating the mixture of step (a'), and
(c') recovering as a solid a cationic [rhodium arene phosphorus ligand] complex or a cationic [rhodium (phosphorus ligand)$_2$] complex.

\* \* \* \* \*

UNITED STATES PATENT AND TRADEMARK OFFICE
CERTIFICATE OF CORRECTION

PATENT NO.      : 8,546,570 B2
APPLICATION NO. : 13/002434
DATED           : October 1, 2013
INVENTOR(S)     : Hans Guenter Nedden It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 157 days.

Signed and Sealed this

Fifteenth Day of September, 2015

Michelle K. Lee
*Director of the United States Patent and Trademark Office*